(12) United States Patent
Wormington et al.

(10) Patent No.: US 8,687,766 B2
(45) Date of Patent: Apr. 1, 2014

(54) ENHANCING ACCURACY OF FAST HIGH-RESOLUTION X-RAY DIFFRACTOMETRY

(75) Inventors: Matthew Wormington, Littleton, CO (US); Alexander Krohmal, Haifa (IL); David Berman, Tivon (IL); Gennady Openganden, Kiryat Yam (IL)

(73) Assignee: Jordan Valley Semiconductors Ltd., Migdal Ha'Emek (IL)

(*) Notice: Subject to any disclaimer, the term of this patent is extended or adjusted under 35 U.S.C. 154(b) by 194 days.

(21) Appl. No.: 13/180,568

(22) Filed: Jul. 12, 2011

(65) Prior Publication Data

US 2012/0014508 A1 Jan. 19, 2012

Related U.S. Application Data

(60) Provisional application No. 61/363,653, filed on Jul. 13, 2010.

(51) Int. Cl.
*G01N 23/20* (2006.01)
*G01T 1/24* (2006.01)

(52) U.S. Cl.
USPC .............................. 378/71; 378/70

(58) Field of Classification Search
None
See application file for complete search history.

(56) References Cited

U.S. PATENT DOCUMENTS

| | | |
|---|---|---|
| 2,805,342 A | 9/1957 | Lang |
| 4,242,588 A | 12/1980 | Silk et al. |
| 4,446,568 A | 5/1984 | Williams et al. |
| 4,696,024 A | 9/1987 | Pesch |
| 4,725,963 A | 2/1988 | Taylor et al. |
| 4,847,882 A | 7/1989 | Knoth et al. |
| 4,989,226 A | 1/1991 | Woodbury et al. |
| 4,995,062 A | 2/1991 | Schulze-Ganzlin et al. |
| 5,151,588 A | 9/1992 | Kiri et al. |
| 5,340,988 A | 8/1994 | Kingsley et al. |
| 5,373,544 A | 12/1994 | Goebel |
| 5,481,109 A | 1/1996 | Ninomiya et al. |
| 5,530,732 A | 6/1996 | Takemi |
| 5,574,284 A | 11/1996 | Farr |
| 5,619,548 A | 4/1997 | Koppel |
| 5,665,969 A | 9/1997 | Beusch |
| 5,711,835 A | 1/1998 | Dona et al. |

(Continued)

FOREIGN PATENT DOCUMENTS

| | | | |
|---|---|---|---|
| JP | 3075548 A | 3/1991 |
| JP | 5188019 A | 7/1993 |

(Continued)

OTHER PUBLICATIONS

He, B., "Two-dimensional X-ray Diffraction", pp. 356-359, Published by John Wiley & Sons, Inc., USA, 2009.

(Continued)

*Primary Examiner* — Hoon Song
*Assistant Examiner* — Danielle Fox
(74) *Attorney, Agent, or Firm* — D. Kligler I.P. Services Ltd.

(57) ABSTRACT

A method for analysis includes directing a converging beam of X-rays toward a surface of a sample and sensing the X-rays that are diffracted from the sample while resolving the sensed X-rays as a function of angle so as to generate a diffraction spectrum of the sample. The diffraction spectrum is corrected to compensate for a non-uniform property of the converging beam.

18 Claims, 8 Drawing Sheets

(56) References Cited

U.S. PATENT DOCUMENTS

| | | | |
|---|---|---|---|
| 5,740,226 A | 4/1998 | Komiya et al. | |
| 5,742,659 A | 4/1998 | Atac et al. | |
| 5,850,425 A | 12/1998 | Wilkins | |
| 5,886,353 A | 3/1999 | Spivey et al. | |
| 5,900,645 A | 5/1999 | Yamada | |
| 5,923,720 A | 7/1999 | Barton et al. | |
| 5,949,847 A | 9/1999 | Terada et al. | |
| 5,963,329 A | 10/1999 | Conrad et al. | |
| 6,041,098 A | 3/2000 | Touryanski et al. | |
| 6,192,103 B1 | 2/2001 | Wormington et al. | |
| 6,226,347 B1 | 5/2001 | Golenhofen | |
| 6,226,349 B1 | 5/2001 | Schuster et al. | |
| 6,317,483 B1 | 11/2001 | Chen | |
| 6,331,890 B1 | 12/2001 | Marumo et al. | |
| 6,381,303 B1 | 4/2002 | Vu et al. | |
| 6,389,102 B2 | 5/2002 | Mazor et al. | |
| 6,453,006 B1 | 9/2002 | Koppel et al. | |
| 6,459,763 B1 | 10/2002 | Koinuma et al. | |
| 6,504,902 B2 | 1/2003 | Iwasaki et al. | |
| 6,507,634 B1 | 1/2003 | Koppel et al. | |
| 6,512,814 B2 | 1/2003 | Yokhin et al. | |
| 6,556,652 B1 | 4/2003 | Mazor et al. | |
| 6,574,305 B2 | 6/2003 | Boer et al. | |
| 6,625,250 B2 | 9/2003 | Houge | |
| 6,639,968 B2 | 10/2003 | Yokhin et al. | |
| 6,643,354 B2 | 11/2003 | Koppel et al. | |
| 6,665,372 B2 | 12/2003 | Bahr et al. | |
| 6,680,996 B2 | 1/2004 | Yokhin et al. | |
| 6,711,232 B1 | 3/2004 | Janik | |
| 6,718,008 B1 | 4/2004 | He et al. | |
| 6,744,850 B2 | 6/2004 | Fanton et al. | |
| 6,744,950 B2 | 6/2004 | Aleksoff | |
| 6,750,952 B2 | 6/2004 | Grodnensky et al. | |
| 6,754,304 B1 | 6/2004 | Kumakhov | |
| 6,754,305 B1 | 6/2004 | Rosencwaig et al. | |
| 6,768,785 B2 | 7/2004 | Koppel et al. | |
| 6,771,735 B2 | 8/2004 | Janik et al. | |
| 6,807,251 B2 | 10/2004 | Okanda et al. | |
| 6,810,105 B2 | 10/2004 | Nasser-Ghodsi et al. | |
| 6,813,338 B2 | 11/2004 | Takata et al. | |
| 6,879,051 B1 | 4/2005 | Singh et al. | |
| 6,895,075 B2 | 5/2005 | Yokhin et al. | |
| 6,898,270 B2 | 5/2005 | Lange et al. | |
| 6,937,694 B2 | 8/2005 | Yokoyama et al. | |
| 6,947,520 B2 | 9/2005 | Yokhin et al. | |
| 6,963,630 B2 | 11/2005 | Umezawa et al. | |
| 6,970,532 B2 | 11/2005 | Hayashi et al. | |
| 6,987,832 B2 | 1/2006 | Koppel et al. | |
| 6,996,208 B2 | 2/2006 | Helming et al. | |
| 6,999,557 B2 | 2/2006 | Yamaguchi et al. | |
| 7,003,075 B2 | 2/2006 | Miyake et al. | |
| 7,035,373 B2 | 4/2006 | Omote | |
| 7,062,013 B2 | 6/2006 | Berman et al. | |
| 7,068,753 B2 | 6/2006 | Berman et al. | |
| 7,076,024 B2 | 7/2006 | Yokhin | |
| 7,110,491 B2 | 9/2006 | Mazor et al. | |
| 7,113,566 B1 | 9/2006 | Peled et al. | |
| 7,116,754 B2 | 10/2006 | Lischka et al. | |
| 7,120,227 B2 | 10/2006 | Ozawa et al. | |
| 7,120,228 B2 | 10/2006 | Yokhin et al. | |
| 7,158,608 B2 | 1/2007 | Kucharczyk | |
| 7,213,686 B2 | 5/2007 | Kaufman | |
| 7,231,016 B2 | 6/2007 | Berman et al. | |
| 7,242,743 B2 | 7/2007 | Fewster | |
| 7,242,745 B2 | 7/2007 | He et al. | |
| 7,258,485 B2 | 8/2007 | Nakano et al. | |
| 7,406,153 B2 | 7/2008 | Berman | |
| 7,474,732 B2 | 1/2009 | Berman et al. | |
| 7,483,513 B2 | 1/2009 | Mazor et al. | |
| 7,551,719 B2 | 6/2009 | Yokhin et al. | |
| 7,742,564 B2 | 6/2010 | Parham et al. | |
| 2001/0033995 A1* | 10/2001 | Tanaka et al. | 430/311 |
| 2003/0123610 A1 | 7/2003 | Okanda et al. | |
| 2003/0157559 A1 | 8/2003 | Omote et al. | |
| 2004/0132262 A1* | 7/2004 | Ayabe et al. | 438/428 |
| 2005/0195941 A1* | 9/2005 | Lischka et al. | 378/71 |
| 2005/0236573 A1* | 10/2005 | Vogtmeier | 250/370.09 |
| 2006/0115046 A1* | 6/2006 | Berman et al. | 378/70 |
| 2011/0164730 A1 | 7/2011 | Yokhin et al. | |

FOREIGN PATENT DOCUMENTS

| | | |
|---|---|---|
| JP | 666741 A | 3/1994 |
| JP | 6258260 A | 9/1994 |
| JP | 6273357 A | 9/1994 |
| JP | 7311163 A | 11/1995 |
| JP | 8-313458 A | 11/1996 |
| JP | 9210663 A | 8/1997 |
| JP | 9-229879 A | 9/1997 |
| JP | 10048398 A | 2/1998 |
| JP | 10160688 A | 6/1998 |
| JP | 10206354 A | 8/1998 |
| JP | 10318949 A | 12/1998 |
| JP | 1114562 A | 1/1999 |
| JP | 11014561 A | 1/1999 |
| JP | 11304728 A | 11/1999 |
| JP | 200088776 A | 3/2000 |
| JP | 2000266698 A | 9/2000 |
| JP | 2000292379 A | 10/2000 |
| JP | 2000314708 A | 11/2000 |
| JP | 200166398 A | 3/2001 |
| JP | 2001153822 A | 6/2001 |
| JP | 2003194741 A | 7/2003 |
| JP | 2003329619 A | 11/2003 |
| JP | 2004257914 A | 9/2004 |
| JP | 2005172830 A | 6/2005 |
| JP | 2005214712 A | 8/2005 |
| JP | 2005265841 A | 9/2005 |
| JP | 2005315742 A | 11/2005 |
| JP | 2005326261 A | 11/2005 |
| JP | 2006317249 A | 11/2006 |
| WO | 2004013867 A2 | 2/2004 |

OTHER PUBLICATIONS

Bowen et al., "X-Ray metrology by Diffraction and Reflectivity," CP550, Characterization and Metrology for ULSI Technology: 2000 International Conference, pp. 570-579, American Institute of Physics, 2001.

Cohen et al., "Characterization of the silicon on insulator film in bonded wafers by high resolution x-ray diffraction", Applied Physics Letters, vol. 75, No. 6, pp. 787-789, Aug. 9, 1999.

Cohen et al., "High-Resolution X-Ray Diffraction for Characterization and Monitoring of Silicon-on-Insulator Fabrication Processes," Journal of Applied Physics, vol. 93, No. 1, pp. 245-250, Jan. 1, 2003.

Goorsky et al., "Grazing Incidence In-plane Diffraction Measurement of In-plane Mosaic with Microfocus X-ray Tubes", Crystal Research and Technology, vol. 37, No. 7, pp. 645-653, year 2002.

Hayashi et al., "Refracted X-Rays Propagating Near the Surface under Grazing Incidence Condition," Spectrochimica Acta, Part B 54, pp. 227-230, year 1999.

Hu et al., "Small angle x-ray scattering metrology for sidewall angle and cross section of nanometer scale line gratings," Journal of Applied Physics, vol. 96, No. 4, pp. 1983-1987, Aug. 15, 2004.

Guerault, H., "Specular reflectivity and off-specular scattering: Tools for roughness investigation", Instituut voor Kern—en Stralingsfysica, Dec. 15, 2000.

Jones et al., "3-Dimensional Lineshape Metrology Using Small Angle X-ray Scattering", AIP Conference Proceedings, vol. 683, pp. 434-438, Sep. 30, 2003.

Jones et al., "Sub-Nanometer Wavelength Metrology of Lithographically Prepared Structures: A Comparison of Neutron and X-Ray Scattering", Proceedings of SPIE—The International Society for Optical Engineering, Jun. 1, 2003.

Jones et al., "Small Angle X-ray Scattering for Ssub-100 nm Pattern Characterization," Applied Physics Letters, vol. 83, No. 19, pp. 4059-4061, Nov. 10, 2003.

Jordan Valley, "How to Measure SiGe on SOI on BedeMetrixTM Tools", Electronic Materials Conference 2008, USA, Jul. 21, 2008.

(56) References Cited

OTHER PUBLICATIONS

Kojima et al., "Structural Characterization of Thin Films by X-ray Reflectivity," Rigaku Journal, vol. 16, No. 2, pp. 31-41, year 1999.
Kozaczek et al., "X-ray Diffraction Metrology for 200mm Process Qualification and Stability Assessment," Advanced Metallization Conference, Canada, Oct. 8-11, 2001.
X-Ray Optical Systems, Inc., "Monolithic Polycapillary Lens Information", Albany, USA, Dec. 29, 1998.
Wu et al., "Substepping and its Application to HST Imaging", Astronomical Data Analysis Software and Systems VII ASP Conference Series, vol. 145, pp. 82-85, year 1998.
Naudon et al., "New Apparatus for Grazing X-ray Reflectometry in the Angle-Resolved Dispersive Mode," Journal of Applied Crystallography, vol. 22, pp. 460-464, year 1989.
Neissendorfer et al., "The Energy-Dispersive Reflectometer/Diffractometer at BESSY-I", Measurement Science Technology, vol. 10, pp. 354-361, IOP Publishing Ltd., year 1999.
Parrill et al., "GISAXS—Glancing Incidence Small Angle X-ray Scattering," Journal de Physique IV, vol. 3, pp. 411-417, Dec. 1993.
Powell et al., "X-ray Diffraction and Reflectivity Characterization of SiGe Superlattice", Semiconductor Science Technology Journal, vol. 7, pp. 627-631, year 1992.
Di Fonzo et al., "Non-Destructive Determination of Local Strain with 100-Nanometre Spatial Resolution," Nature, vol. 403, pp. 638-640, Feb. 10, 2000.
Ulyanenkov, A., "Introduction to High Resolution X-Ray Diffraction," Workshop on X-ray characterization of thin layers, Uckley, May 21-23, 2003.
Authier, A., "Dynamical Theory of X-Ray Diffraction", International Union of Crystallography, Monographs on Crystallography 11, revised edition, pp. 101-102, Oxford University Press 2005.
Wiener et al., "Characterization of Titanium Nitride Layers by Grazing—Emission X-Ray Fluorescence Spectrometry", Applied Surface Science, vol. 125, pp. 129-136, Elsevier Science BV 1998.
Woitok et al., "Towards Fast Reciprocal Space Mapping," JCPDS—International Centre for Diffraction Data, Advances in X-ray Analysis, vol. 48, pp. 165-169, year 2005.
Oxford Instruments Inc., Series 5000 Model XTF5011 X-Ray Tube Datasheet, Scotts Valley, USA, Jun. 28, 2000.
Japanese Patent Application # 2003549898 Official Action dated Jun. 7, 2010.
U.S. Appl. No. 09/941,723 Official Action dated Apr. 4, 2005.
U.S. Appl. No. 10/946,426 Official Action dated Feb. 6, 2006.
U.S. Appl. No. 11/018,352 Official Action dated Feb. 8, 2006.
U.S. Appl. No. 11/018,352 Official Action dated Oct. 24, 2005.
U.S. Appl. No. 11/200,857 Official Action dated Aug. 11, 2008.
U.S. Appl. No. 11/200,857 Official Action dated Aug. 27, 2007.
U.S. Appl. No. 11/200,857 Official Action dated Mar. 11, 2008.
U.S. Appl. No. 11/389,490 Official Action dated May 1, 2008.
U.S. Appl. No. 11/487,433 Official Action dated May 29, 2008.
U.S. Appl. No. 61/328,645, filed Apr. 28, 2010.
Japanese Patent Application # 2005274293 Official Action dated Dec. 21, 2010.
Japanese Patent Application # 2005273641 Official Action dated Oct. 28, 2010.
Pesek et al., "Lattice Misfit and Relative Tilt of Lattice Planes in Semiconductor Heterostructures", Semiconductor Science and Technology Journal, vol. 6, pp. 705-708, IOP Publishing Ltd 1991.
Japanese Patent Application # 2006114489 Official Action dated Nov. 30, 2010.
Japanese Patent Application # 2006114489 Official Action dated Jun. 14, 2011.
Japanese Patent Application # 2006194756 Official Action dated Jul. 26, 2011.
U.S. Appl. No. 12/958,420, filed on Dec. 2, 2010.
Korean Patent Application # 10-2005-0083542 Office Action dated Feb. 15, 2012.
U.S. Appl. No. 12/683,436 Office Action dated Jan. 23, 2012.
U.S. Appl. No. 13/913,444 Office Action dated Aug. 2, 2013.
Krohmal, A., U.S. Appl. No. 13/913,444, filed Jun. 9, 2013.

* cited by examiner

ENHANCING ACCURACY OF FAST HIGH-RESOLUTION X-RAY DIFFRACTOMETRY

CROSS-REFERENCE TO RELATED APPLICATION

This application claims the benefit of U.S. Provisional Patent Application 61/363,653, filed Jul. 13, 2010, which is incorporated herein by reference.

FIELD OF THE INVENTION

The present invention relates generally to X-ray analysis, and specifically to measurements of high-resolution X-ray diffraction.

BACKGROUND OF THE INVENTION

X-ray diffractometry (XRD) is a well-known technique for studying the crystalline structure of matter. In XRD, a sample is irradiated by a monochromatic X-ray beam, and the locations and intensities of the diffraction peaks are measured. The characteristic diffraction angles and the intensity of the diffracted radiation depend on the lattice planes of the sample under study and the atoms that make up the crystalline material. For a given wavelength λ and lattice plane spacing d, diffraction peaks will be observed when the X-ray beam is incident on a lattice plane at angles θ that satisfy the Bragg condition: $\lambda = 2d \sin \theta_B$. The angle $\theta_B$ that satisfies the Bragg condition is known as the Bragg angle. Distortions in the lattice planes due to stress, solid solution, defects or other effects lead to observable changes in the XRD spectrum.

XRD has been used, inter alia, for measuring characteristics of crystalline layers produced on semiconductor wafers. For example, U.S. Pat. No. 7,120,228, whose disclosure is incorporated herein by reference, describes a combined X-ray reflectometer and diffractometer. The described apparatus includes a radiation source, which is adapted to direct a converging beam of X-rays toward a surface of the sample. At least one detector array is arranged to sense the X-rays scattered from the sample as a function of elevation angle over a range of elevation angles simultaneously. In one configuration, the detector array senses the X-rays that are diffracted from the surface in a vicinity of a Bragg angle of the sample. A signal processor processes the output signals from the detector array so as to determine a characteristic of the surface layer of the sample.

Other systems for XRD measurement are described, for example, in U.S. Pat. Nos. 7,076,024 and 7,551,719, whose disclosures are also incorporated herein by reference.

SUMMARY

Embodiments of the present invention that are described hereinbelow provide techniques that may be used to enhance the accuracy of X-ray scattering measurements, and particularly of fast, high-resolution XRD (HRXRD).

There is therefore provided, in accordance with an embodiment of the present invention, a method for analysis, which includes directing a converging beam of X-rays toward a surface of a sample and sensing the X-rays that are diffracted from the sample while resolving the sensed X-rays as a function of angle so as to generate a diffraction spectrum of the sample. The diffraction spectrum is corrected to compensate for a non-uniform property of the converging beam.

In some embodiments, correcting the diffraction spectrum includes modifying an angular scale of the diffraction spectrum. Modifying the angular scale may include adjusting the angular scale to compensate for an aberration in the converging beam. Typically, adjusting the angular scale includes calibrating a relation between an angle of the diffracted X-rays and an angular step size in the diffraction spectrum, and applying the calibrated relation to correct the angular scale of the diffraction spectrum. Further additionally or alternatively, correcting the diffraction spectrum includes modifying the intensity in the diffraction spectrum. Modifying the intensities may include applying an intensity correction as a function of the angle of the sensed X-rays in order to compensate for a non-uniform intensity of the converging beam.

In some embodiments, the method includes analyzing the diffraction spectrum so as to identify a characteristic of the sample. In one embodiment, the sample includes an epitaxial layer that is formed over a substrate, and the diffraction spectrum includes at least a first diffraction peak due to the substrate and a second diffraction peak due to the epitaxial layer, and analyzing the diffraction spectrum includes applying the corrected diffraction spectrum in finding an angular distance between the first and second diffraction peaks.

There is also provided, in accordance with an embodiment of the present invention, a method for analysis, which includes directing a converging beam of X-rays toward a surface of a sample including an epitaxial layer that is formed over a substrate. The X-rays that are diffracted from the epitaxial layers and from the substrate are sensed simultaneously while resolving the sensed X-rays as a function of angle so as to generate a diffraction spectrum including at least a first diffraction peak due to the substrate and a second diffraction peak due to the epitaxial layer. An angular distance between the first and second diffraction peaks is found while correcting the diffraction spectrum to account for a depth of penetration of the X-rays into the substrate.

Correcting the diffraction spectrum may include computing a shift of the first diffraction peak due to the penetration as a function of angles of incidence and diffraction of the X-rays.

There is additionally provided, in accordance with an embodiment of the present invention, an X-ray detector assembly, including an integrated circuit, which includes an array of detector elements and a readout circuit, adjacent to the array and coupled to read charge out of the detector elements. A non-metallic shield is positioned over the readout circuit so as to prevent X-rays from striking the readout circuit.

In a disclosed embodiment, the shield includes a monocrystalline material, which is oriented so that X-rays diffracted from the shield are directed away from the readout circuit. Alternatively or additionally, the shield may include an amorphous material.

There is further provided, in accordance with an embodiment of the present invention, apparatus for analysis, including an X-ray source, which is configured to direct a converging beam of X-rays toward a surface of a sample. A detector assembly is configured to sense the X-rays that are diffracted from the sample while resolving the sensed X-rays as a function of angle so as to generate a diffraction spectrum of the sample. A processor is coupled to correct the diffraction spectrum to compensate for a non-uniform property of the converging beam.

There is moreover provided, in accordance with an embodiment of the present invention, apparatus for analysis, including an X-ray source, which is configured to direct a converging beam of X-rays toward a surface of a sample including an epitaxial layer that is formed over a substrate. A detector assembly is configured to sense simultaneously the X-rays that are diffracted from the epitaxial layer and from the substrate while resolving the sensed X-rays as a function of angle so as to generate a diffraction spectrum including at least a first diffraction peak due to the substrate and a second diffraction peak due to the epitaxial layer. A processor is configured to find an angular distance between the first and second diffraction peaks while correcting the diffraction spectrum to account for a depth of penetration of the X-rays into the substrate.

The present invention will be more fully understood from the following detailed description of the embodiments thereof, taken together with the drawings in which:

DETAILED DESCRIPTION OF EMBODIMENTS

Overview

High-resolution X-ray diffraction (HRXRD) can be used to provide detailed information regarding the structure and composition of thin film layers, such as epitaxial layers formed on silicon wafers in manufacturing of semiconductor devices. The technique is described generally in the above-mentioned U.S. patents.

Because of the very small scale and high precision required in semiconductor device production, it is desirable to use a finely-focused X-ray beam to irradiate the sample under test, and to measure the diffracted X-rays using a tightly-controlled optical system. Even under these conditions, however, optical and geometrical factors can distort the measurement results and reduce accuracy. Embodiments of the present invention that are described hereinbelow provide methods for estimating and correcting the diffraction spectrum for a number of these factors and thus enhancing the accuracy of HRXRD measurements. The correction to the diffraction spectrum may be in the form of adjustments to the angular and/or intensity scale of the measured spectrum itself, or as adjustments in a model of sample properties that is fitted to the measured spectrum.

In some embodiments of the present invention, an X-ray source directs a converging beam of X-rays toward the surface of a sample, such as a semiconductor wafer. A detector array senses the X-rays that are diffracted from the sample while resolving the sensed X-rays as a function of angle so as to generate a diffraction spectrum of the sample. A processor then corrects the diffraction spectrum to compensate for non-uniformities of the converging beam.

The corrections applied by the processor may include modifying the angular scale of the diffraction spectrum, particularly to compensate for aberrations in the converging beam. The angular locations of the peaks in the diffraction spectrum are a key indicator of the properties of the sample, and correction of errors in the angular scale thus has a direct impact on improving the accuracy of measurement of the sample properties.

Additionally or alternatively, the processor may modify the intensities in the diffraction spectrum in order to compensate for a non-uniform intensity of the converging beam as a function of the angle. The observed intensity distribution in the spectrum may also depend on the size of the test pad from which diffracted X-rays are received, because aberrations can cause some of the intensity to fall outside of the pad. This phenomenon can be measured during the setup and characterization of the measurement system and then applied during measurements.

Further additionally or alternatively, the processor may correct the diffraction spectrum to account for apparent angular shifts of the peaks in the spectrum that are related to the depth of penetration of the X-rays into the substrate of the sample.

System Description

Figure 1:
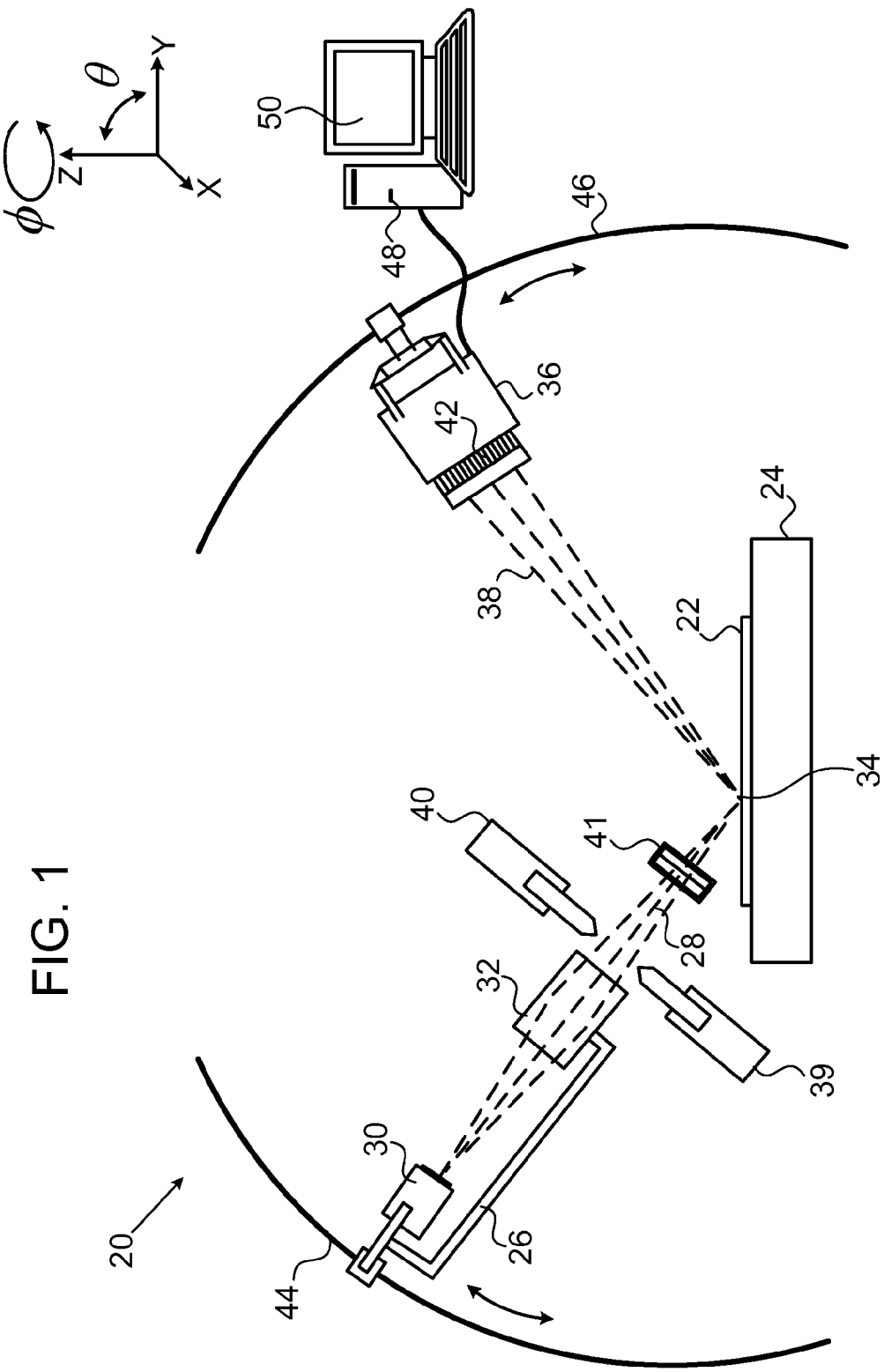
FIG. 1 is a schematic side view of an X-ray metrology system, in accordance with an embodiment of the present invention.

FIG. 1 is a schematic side view of a system 20 for HRXRD of a sample 22, in accordance with an embodiment of the present invention. Sample 22 may comprise, for example, a semiconductor wafer with one or more epitaxial layers formed over the wafer surface. The sample is mounted on a motion stage 24, allowing accurate adjustment of the position and orientation of the sample. An X-ray source 26 directs a converging X-ray beam 28 toward a small area 34 on sample 22. Typically, source 26 comprises an X-ray tube 30 with suitable optics 32 to focus and monochromatize beam 28. Beam 28 typically subtends at least 2°, and may subtend as much as 4° or even more, depending on optics 32, in order to irradiate sample 22 over a large range of angles simultaneously.

X-rays are diffracted from sample 22 in a generally diverging beam 38, which is received by a detector assembly 36. The detector assembly typically comprises a detector array 42, such as a CCD array, comprising multiple detector elements, configured so as to resolve beam 38 as a function of elevation angle θ. Typically, the angular span of array 42 is comparable to that of beam 28, i.e., at least 2°, and possibly 4° or greater. Various types of X-ray sources and detector assemblies may be used in system 20. Details of such components are described, for example, in the above-mentioned U.S. Pat. Nos. 7,076,024, 7,120,228 and 7,551,719.

Beam blockers 39 and 40 (such as a knife edges) and/or other optical elements may be used to limit beam 28 and/or beam 38 and to block undesired scattered radiation that might otherwise strike array 42 and interfere with the diffraction measurement. Another beam blocker 41, oriented perpendicularly to blockers 39 and 40, is used to block undesired irradiation wavelengths. System 20 may also comprise other X-ray optical elements (not shown in the figures) for improving beam quality and reducing background radiation, as described, for example, in U.S. patent application Ser. No. 12/683,436, filed Jan. 7, 2010, whose disclosure is incorporated herein by reference.

The positions of source 26 and detector assembly 36 are controlled by motion assemblies 44 and 46, respectively. In the simplified view shown in FIG. 1, the motion assemblies comprise curved tracks, which permit the source and detector assembly to be positioned at the appropriate elevations, typically in the vicinity of the Bragg angles of the layers that are to be analyzed. Other suitable motion assemblies will be apparent to those skilled in the art. For the sake of this example, it is assumed that the lattice planes creating the diffraction pattern are approximately parallel to the surface of sample 22, so that the incidence and takeoff angles defined by beams 28 and 38 relative to the surface are both equal to the Bragg angle. Alternatively, source 26 and detector assembly 38 may be positioned at different incidence and takeoff angles in order to measure diffraction from lattice planes that are not parallel to the surface of sample 22.

In addition, as noted above, stage 24 may be configured to translate the X-Y location on the sample that falls within area 34, as well as to rotate the azimuthal angle $\phi$ of the sample relative to beam 28. (As shown in FIG. 1, the X-Y plane is taken to be the sample surface, with the Z-axis perpendicular to the surface; $\theta$ is the elevation angle relative to the Z-axis; and $\phi$ is the azimuthal angle of rotation about the Z-axis.)

A signal processor 48 receives and analyzes the output of assembly 36, so as to measure a spectrum 50 of the flux of X-ray photons diffracted from sample 22 as a function of angle at a given energy or over a range of energies. Processor 48 may also adjust the positions and operating parameters of the other components of system 20, including source 26, detector assembly 36, stage 24, and motion assemblies 44 and 46.

Typically, sample 22 has one or more thin surface layers, such as thin films, at area 34, so that distribution 50 as a function of elevation angle exhibits a structure that is characteristic of diffraction effects due to the surface layer and underlying layers. Processor 48 analyzes the angular spectrum in order to determine characteristics of one or more of the layers of the sample, such as the composition, thickness, lattice strain, relaxation, crystalline quality and/or tilt angle of the layer. For these purposes, the processor may apply methods of analysis such as those described in the above-mentioned U.S. patents and/or in U.S. patent application Ser. No. 12/958,420, filed Dec. 2, 2010, whose disclosure is incorporated herein by reference, as well as other methods that are known in the art.

As part of this analysis, processor 48 corrects certain inaccuracies that may arise in the X-ray measurements due to deviation of the components of system 20 from ideal physical characteristics. These inaccuracies may arise, for example, due to non-uniformity and aberrations in the X-ray beam, as well as variations in the depth of penetration of X-rays into sample 22. Methods for performing these corrections are described in detail hereinbelow.

The components of system 20 and the techniques described herein may be integrated into systems that provide other types of measurement functionality, such as X-ray reflectometry and scattering measurements. Additionally or alternatively, these components and techniques may be integrated as process monitoring tools in manufacturing systems, such as systems for semiconductor wafer fabrication. Integrated systems of these types are described in greater detail in the above-mentioned patents.

Figure 2A:
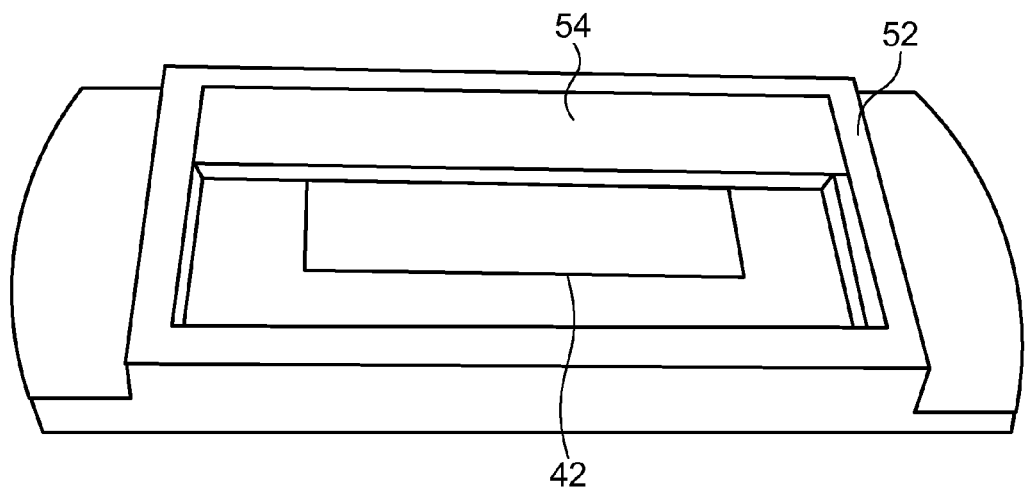
FIG. 2A is a schematic, pictorial illustration of an X-ray detector, in accordance with an embodiment of the present invention.
Figure 2B:
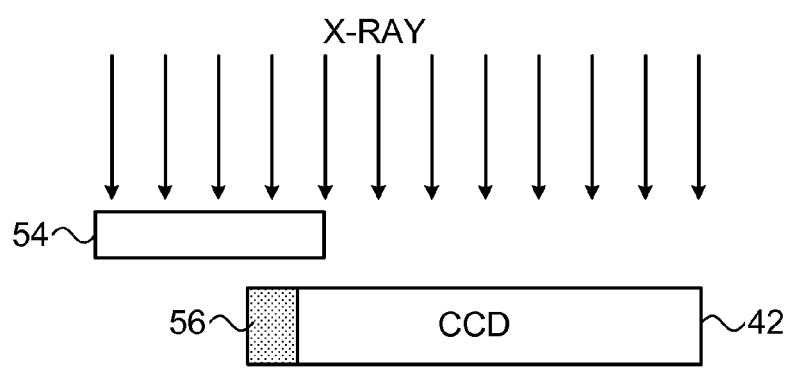
FIG. 2B is a schematic, sectional view of the X-ray detector of FIG. 2A.

FIGS. 2A and 2B schematically illustrate elements of detector assembly 36, showing the use of a shield 54 for blocking background radiation, in accordance with an embodiment of the present invention. FIG. 2A is a pictorial illustration that shows shield 54 and detector array 42 in a device package 52, while FIG. 2B is a sectional illustration showing the relative positions of the shield and array.

Detector array 42 in this embodiment may be, for example, a charge-coupled device (CCD). In such devices, charge is shifted out of the detector elements into a readout circuit comprising a register line 56 near the edge of the device, which then outputs a signal indicative of the charges accumulated (and hence the X-ray intensity sensed) by each detector element. In conventional CCD designs, the register line is exposed to radiation along with the detector elements, and incidence of stray electrons on the register line may result in accumulation of charge in the register line. The inventors have found that this register line charge can be a major contributor to the level of background noise in the output signal from array 42.

To reduce this source of noise, register line 56 is covered by shield 54, which blocks incident X-rays, as shown in FIG. 2B. Typically, the shield is made from a crystalline material, such as a strip cut from a Si or Ge wafer, which is about 0.7 mm thick and may be mounted about 2 mm above the surface of array 42, for instance. The mono-crystalline shield 54 may be oriented so that X-rays diffracted from the shield are angled away from detector array 42. The edge of shield 54 may be polished, typically to a roughness of about 25 µm, for example, to prevent stray reflections and diffraction at the edge. The use of a mono-crystalline shield is superior to metal shields that are used in some applications, since X-rays may diffract from the polycrystalline metal in many directions, some of which will impinge on the detector array. Alternatively, shield 42 may comprise an amorphous material with sufficient X-ray absorbance.

Figure 3:
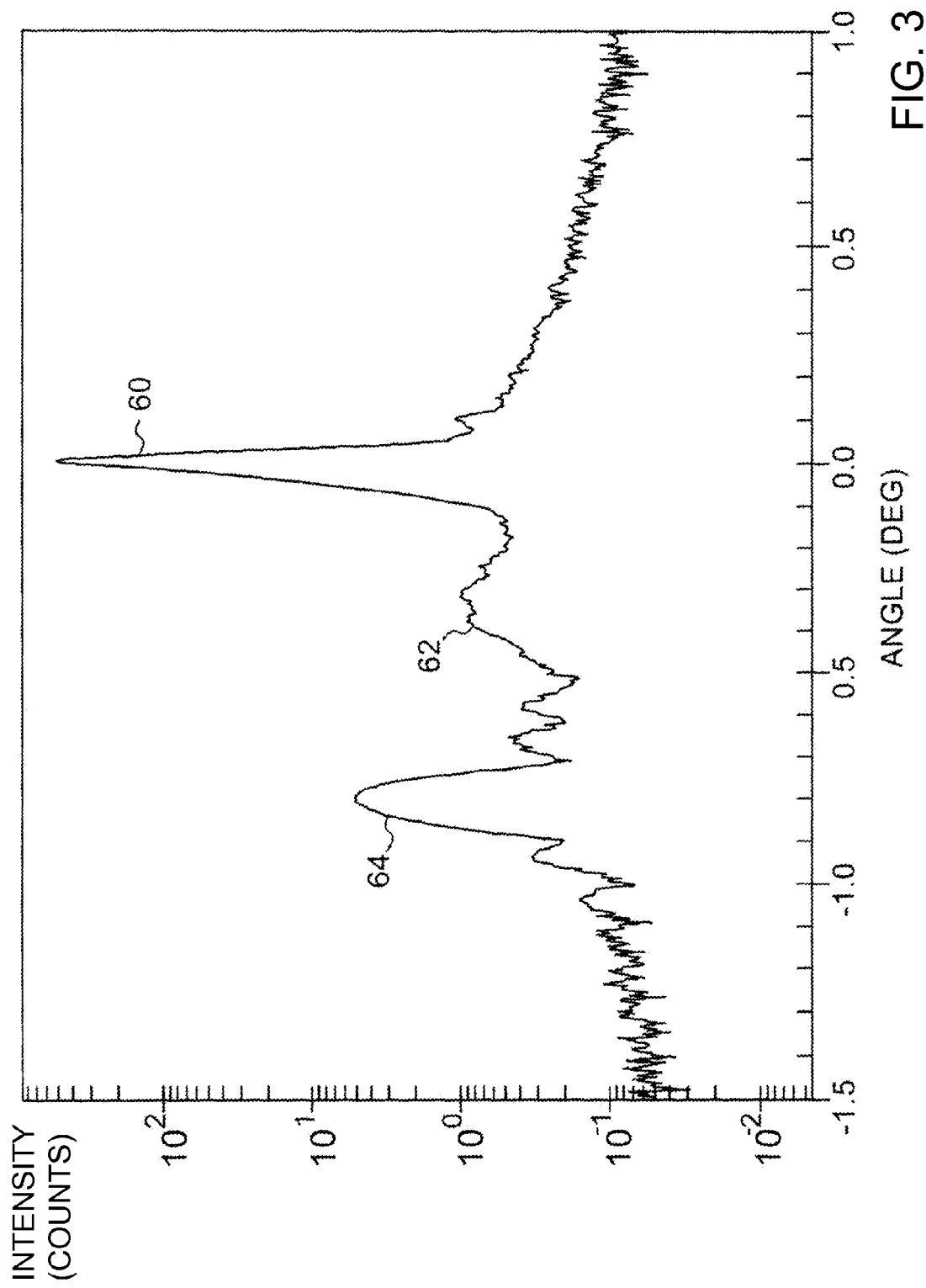
FIG. 3 is a schematic representation of a HRXRD spectrum, in accordance with an embodiment of the present invention.

To align shield 54, array 42 may be irradiated with X-rays while the output signal from the array is monitored. The shield is slid across the array until the signal shows that register line 56 and the last few rows of detector elements adjacent to the register line are blocked. The shield is then fixed in place. The inventors have found that using a mono-crystalline shield in this fashion reduces the background level in the output signal by about an order of magnitude FIG. 3 is a schematic representation of a HRXRD spectrum obtained from sample 22 in system 20, in accordance with an embodiment of the present invention. The spectrum is shown on a logarithmic scale in counts captured by the elements of array 42, as a function of the respective elevation angles of the elements. The angular scale in FIG. 3 is adjusted, for the sake of convenience, so that a peak 60 due to diffraction from the silicon wafer substrate is taken as the origin ($\theta=0$). Additional peaks 62 and 64 arise from epitaxial thin-film layers formed over the substrate. The separation between the peaks can be used, for example, to indicate accurately the properties of the layers.

This particular spectrum is shown only by way of example, and system 20 may similarly be used to perform HDXRD measurements on samples and layers of other types, as will be apparent to those skilled in the art.

Techniques for Accuracy Enhancement

Correcting for Penetration Depth

Figure 4:
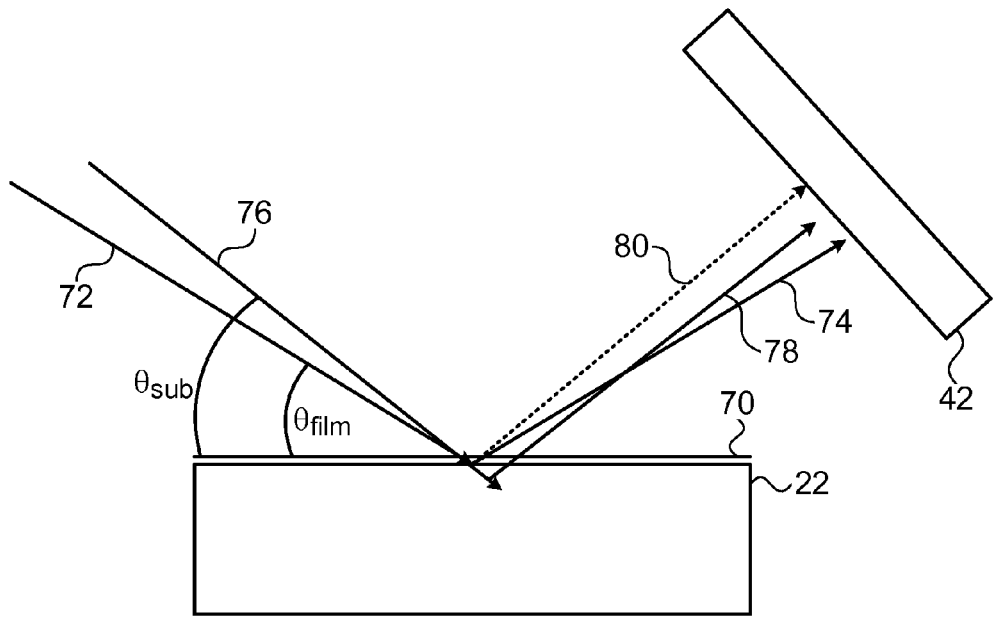
FIG. 4 is a schematic, sectional view of elements of an X-ray metrology system, illustrating how depth effects are handled in HRXRD measurements, in accordance with an embodiment of the present invention.

FIG. 4 is a schematic, sectional view of elements of system 20, illustrating how depth effects are handled in HDXRD measurements, in accordance with an embodiment of the present invention. In this example, a thin-film epitaxial layer 70 is formed on the surface of the silicon substrate of sample 22. Crystalline structures in the epitaxial layer, as well as the substrate itself, diffract the incident X-ray beam at their respective Bragg angles (shown in the figure as $\theta_{sub}$ for a ray 76 incident on the substrate and $\theta_{film}$ for a ray 72 incident on a thin-film epitaxial layer). The angular displacement between the corresponding diffracted rays 78 and 74 is indicative of the composition and lattice conditions of layer 70, as explained above.

As illustrated in FIG. 4, however, the locus of diffraction of the X-rays from layer 70 is above the locus in the substrate of sample 22, leading to an added angular displacement between the respective diffraction peaks. Diffracted ray 74 is the result of diffraction that takes place within a few hundred Å of the surface. The origin of ray 78, on the other hand, is effectively at a depth of a few microns, which results in a shift of the detected position of the main diffraction peak on detector array 42.

Figure 5:
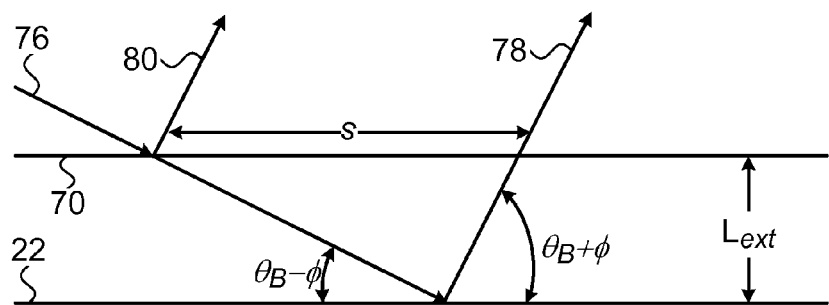
FIG. 5 is a ray diagram showing parameters used in correcting for depth effects, in accordance with an embodiment of the present invention.

FIG. 5 is a ray diagram showing parameters used in correcting for this depth-related shift, in accordance with an embodiment of the present invention. To account for the depth effect in measuring the angular separation between the peaks in the diffraction spectrum, the zero angle in the spectrum (which is normally associated with the substrate peak) is corrected using the parameters shown in the figure. Specifically, referring to FIG. 3, the displacement of peak 60 is calculated based on the parameters shown in FIG. 5, and processor 48 introduces the calculated displacement as a correction into the computation of the inter-peak angular separation in order to compensate for the lateral displacement effect.

The estimated peak displacement s of the substrate diffraction relative to the diffraction from layer 70 is given by the formula:

$$s \approx \frac{L_{ext}}{2}\left[\frac{1}{\tan(\theta_B - \phi)} + \frac{1}{\tan(\theta_B + \phi)}\right] \quad (1)$$

In this formula, $L_{ext}$ is the extinction depth, which can be expressed as twice the penetration depth $z_e$, i.e., $L_{ext}=2z_e$. The penetration depth is defined as the depth in the substrate material at which the X-ray beam amplitude is reduced by attenuation by a factor of e (so that the intensity is reduced by $e^2$) and is given by the formula:

$$z_e = \frac{\lambda\sqrt{\gamma_0|\gamma_h|}}{2\pi\sqrt{\chi_0\chi_h}} \quad (2)$$

Here $\gamma_0$ and $\gamma_h$ are the direction cosines of the incident and diffracted beams, and $\chi_0$ and $\chi_h$ are the electric susceptibilities in the incident and diffracted directions.

The distance traversed by the X-ray beam through the substrate material depends on the Bragg angle $\theta_B$ and, for non-symmetrical reflections, on the offset angle $\phi$. (For symmetrical reflections, $\phi=0$.) The penetration depth depends on these angular factors in a complex way, since the electric susceptibility of the crystalline substrate varies with the directions of the incident and diffracted beams.

Values of the penetration depth can be computed for various reflections and X-ray energies, as described, for example, by Authier in *Dynamical Theory of X-ray Diffraction* (Oxford, 2005), pages 101-102, which are incorporated herein by reference. Table I below presents these values, along with the corresponding peak displacement values, for a number of different reflections from Si(001) substrates using Cu Kα X-rays (approximately 8 keV):

| Reflection | $z_e$ (µm) | s (µm) |
|---|---|---|
| 004 | 1.8 | 5.2 |
| 115 | 4.0 | 8.0 |
| 224 | 2.6 | 9.7 |

As noted above, processor 48 applies the peak displacement s that is listed in the table (or is otherwise computed for the testing conditions of relevance) in adjusting the zero-angle position in the XRD spectrum to offset the depth-related shift. In some cases, this zero-angle adjustment is sufficiently small to be neglected in analyzing the XRD spectrum.

Correcting for Beam Non-Uniformity

Figure 6A:
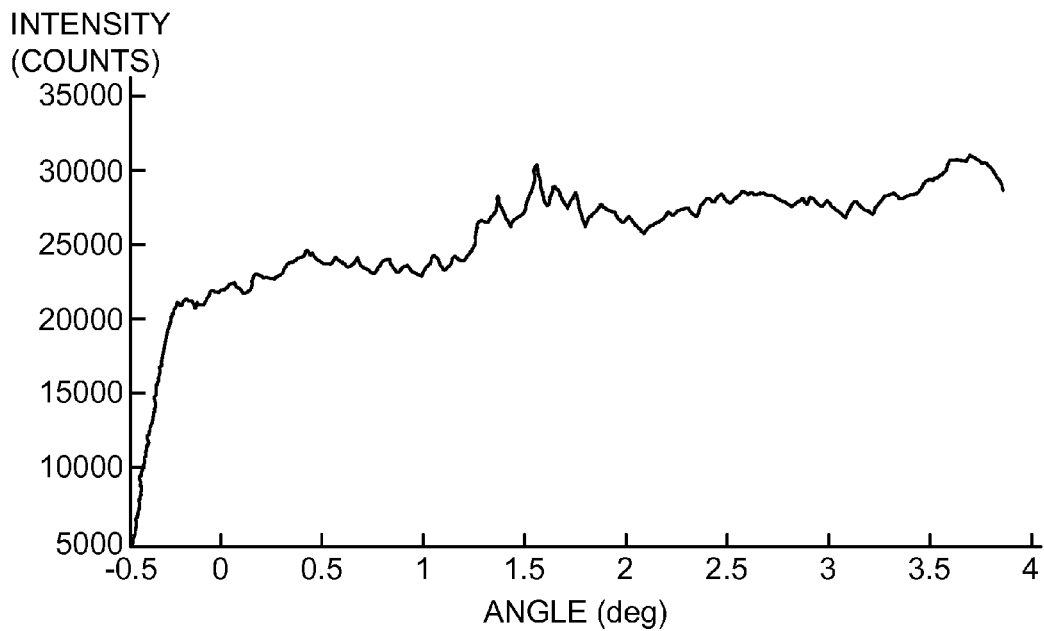
FIG. 6A is a plot of the angular distribution of X-ray beam intensity emitted by an X-ray source in a metrology system.
Figure 6B:
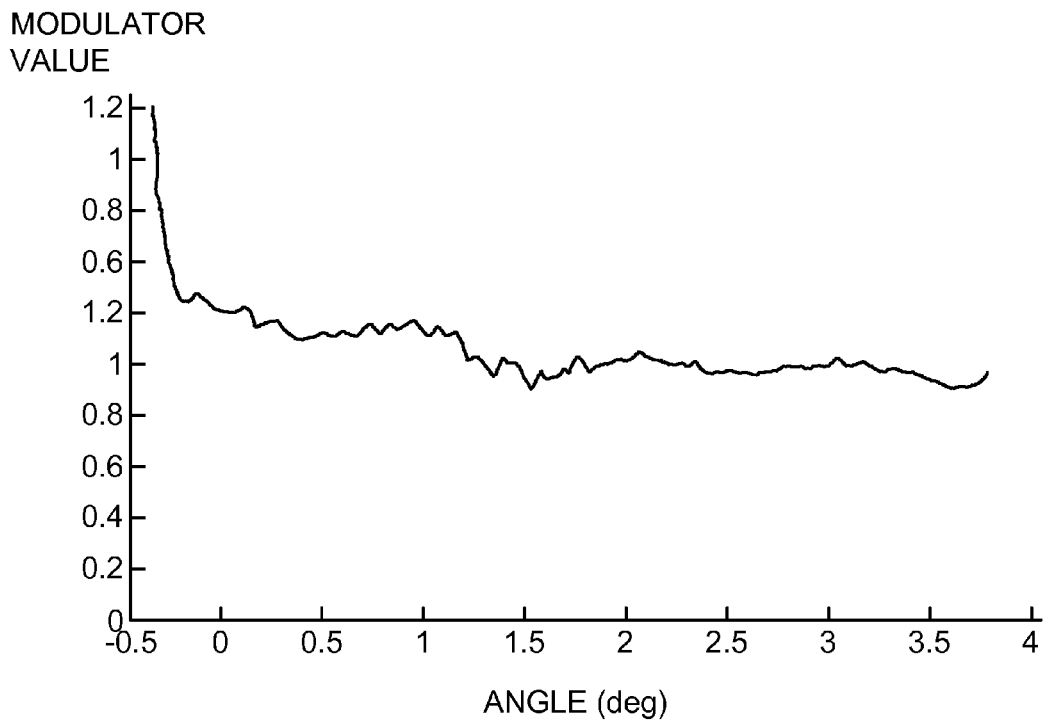
FIG. 6B is a plot of a beam uniformity correction function applied in the metrology system referred to in FIG. 6A, in accordance with an embodiment of the present invention.

FIGS. 6A and 6B schematically illustrate a method for calibrating and correcting for non-uniformity in the intensity distribution of X-ray beam 28 generated by source 26 in system 20, in accordance with an embodiment of the present invention. FIG. 6A is a plot of the actual angular distribution of the intensity emitted by source 26. The non-uniformity of this beam will result in a corresponding intensity measurement error in the raw measurements made by detector assembly 36. FIG. 6B is a plot of a beam uniformity correction function applied by processor 48 in order to compensate for the non-uniformity of the incident beam and thus correct the error.

To compute the correction function of FIG. 6B, the angular dependence of the intensity of beam 28 is measured and calibrated in advance. Detector array 42 can be used for this purpose, by shifting detector assembly 36 to a position in which it receives beam 28 directly from X-ray source 26. In this position, the detector array measures the beam intensity as a function of angle. The output of detector assembly 36 is a vector of intensities y[j], wherein j is the pixel number. (The detector elements in the detector array are also referred to as "pixels.")

To compute the values of the correction function (also referred to as the "modulator function"), and thus to correct the actual diffraction measurements for beam non-uniformity, the elements of the vector y[j] are normalized to be 1 on average. The elements of the modulator function m[j] are calculated according to m[j]=y[j]/Mean(y), wherein Mean(y) denotes the mean value of the intensity in some central region of the angle range, for example from 0.5 to 3.5 degrees. Processor 48 then multiplies the intensities in the HRXRD spectrum obtained from sample 22 by the modulator function values m[i+shift]. The "shift" for a given measurement is the displacement of the substrate (Si) diffraction peak of the substrate from its nominal position (not to be confused with the penetration-related shift value s computed in the preceding section). The angular shift is calculated using the method described in the next section. The shift calculation may also take into account calibration of the zero-angle that takes place during system setup (which is outside the scope of the present patent application).

The method described above assumes that the area from which diffracted X-rays are received is homogeneous, i.e., the entire area has the same layer structure. The effective intensity distribution when measuring diffraction from a small pad can be different, because aberrations can cause some of the irradiating X-rays to fall outside the test pad area, leading to a less uniform effective intensity. Although the present correction procedure is also applicable to small test pads, the modulator function may be adjusted depending on the test pad size.

Compensating for X-Ray Beam Aberrations

Aberrations of X-ray optics 32 may distort beam 28 in both the vertical and horizontal directions. Vertical aberrations (perpendicular to the surface of the sample) can lead to a displacement between the loci of diffraction of substrate diffraction peak 60 and satellite peaks, such as peak 64, arising from epitaxial layers. The amount of aberration as a function of ray angle within the beam can be measured by detecting changes in the X-ray beam incidence location on the sample as a function of the ray angle. (In the absence of aberration, the location should remain constant.) This aberration measurement is then used to model the resulting displacement and its effect on HRXRD measurements, thus generating a correction function to be applied by processor 48.

Once the displacement has been calculated, it can be used by processor 48 either to adjust the scale of the measured spectrum or to introduce a correction into a model of layer properties that is fitted to the measured spectrum. For example, the diffraction angle that is associated with each element in detector array 42 can be corrected for aberration effects, with the result that the diffraction angle is no longer a linear function of position in the detector array. The processor may then use an interpolation function, such as cubic spline interpolation, to convert the detector array output back into a linear angular scale.

Figure 7:
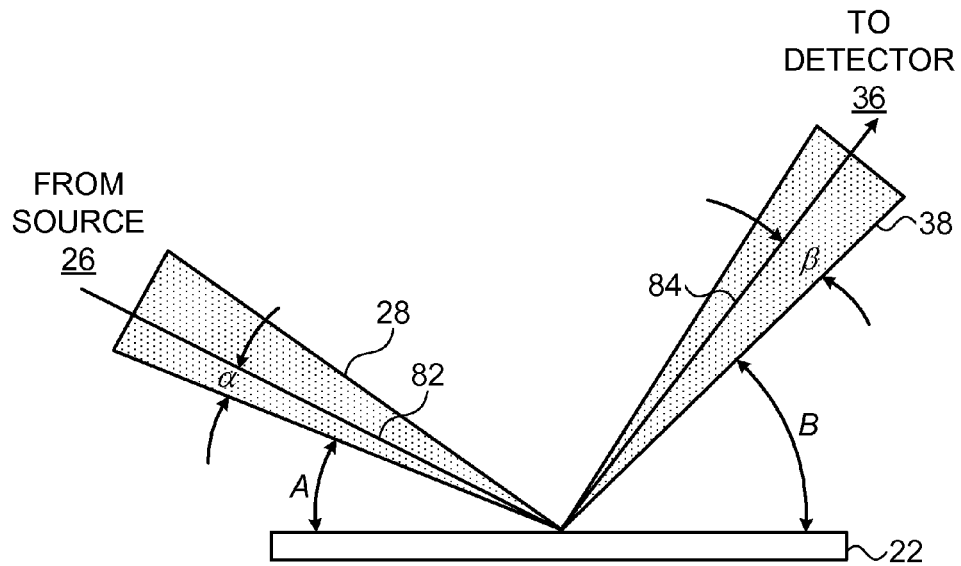
FIG. 7 is a ray diagram showing parameters used in compensating for angle shift in HDXRD measurements, in accordance with an embodiment of the present invention.

FIG. 7 is a ray diagram showing parameters used in compensating for angle shift in HDXRD measurements in system 20, in accordance with an embodiment of the present invention. This shift can vary with the angle A at which X-ray source 26 is position to generate incident beam 28, as well as with the angle B at which detector assembly 36 is positioned in order to capture diffracted beam 38. Each incoming ray 82, at a relative angle $\alpha$ in the incident beam, corresponds to an outgoing ray 84, at a relative angle $\beta$ in the diffracted beam, but the relation between $\alpha$ and $\beta$ can vary with A, B and $\beta$. It is advantageous that processor 48 have an accurate value of $\alpha$ in order to correct properly for beam non-uniformity (as explained above) and aberrations (as will be explained below).

The value of $\alpha$ may be calibrated using the relation:

$$\theta_B = (A+\alpha) + (B+\beta) + \epsilon \quad (3)$$

wherein $\epsilon$ is an error term that represents all of the systematic errors in positioning. This error term may be calibrated during measurement setup and considered to be constant thereafter. To ensure proper calibration, system 20 maintains the sample height at a constant value relative to the beam focus, using a laser triangulation displacement gauge, for example. The error term $\epsilon$ may be measured using the following procedure:

1. Perform a source scan of a Si(001) reference sample with known or small tilt, detecting substrate peak 60 on detector array 42 while stepping the source axis in fine steps, such as 0.05°. If the reference sample has tilt, then the procedure can be repeated at two azimuth rotations of the wafer 180° apart, taking the average of the determined angle values below.
2. Fit the substrate peak intensity for all data in the scan, and plot the fitted peak intensity versus the source-axis angle A to determine the angle $A_0$ that corresponds to the ray angle $\alpha=0$. (Beyond this angle, the detected peak intensity will drop rapidly to zero.)
3. Note the detector axis position $B_0$ of the measurement, and determine the absolute substrate peak position $\beta_0$ for the measurement at the source-axis angle $A_0$.
4. Calculate the error value using the formula:

$$\epsilon = 2\theta_B - A_0 - (B_0 + \beta_0) \quad (4)$$

This procedure allows $\epsilon$ to be determined to an accuracy of about 0.05°. The estimated value of $\epsilon$ can be checked and refined by applying the corrections to the source-axis scan data.

Following this calibration, processor 48 can relate the source angle to the detection angle using the relation $\alpha=k-\beta$, wherein $k=2\theta_B - A - B - \epsilon$. The angle shift to be applied to the correction data for each measurement is then determined from the absolute detection angle $\beta$ by the formula:

$$\text{shift} = \beta - \alpha = 2\beta - k \quad (5)$$

Figure 8:
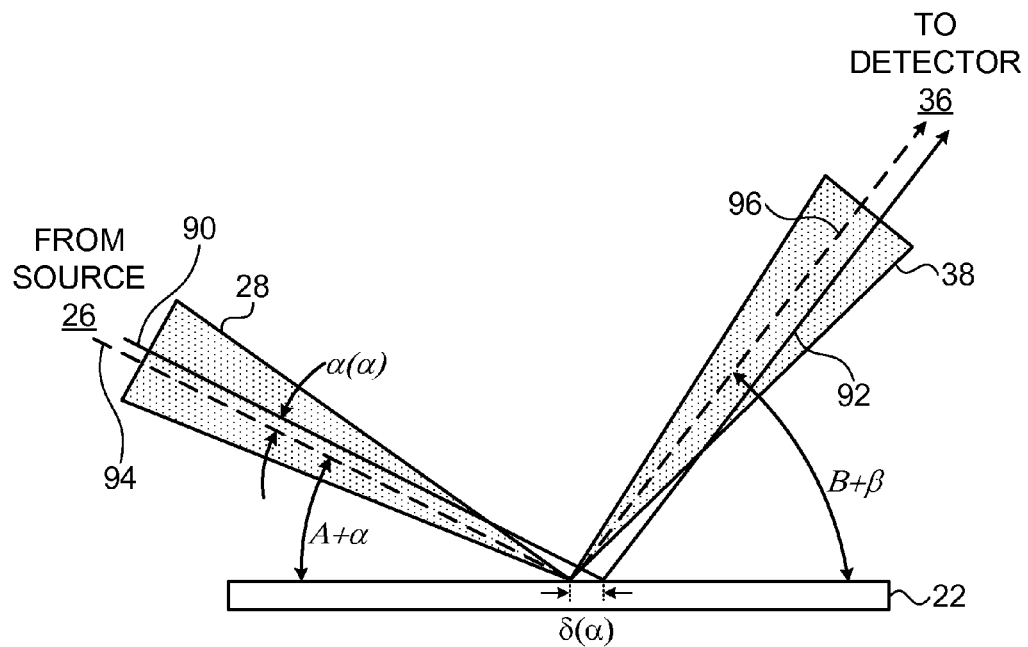
FIG. 8 is a ray diagram showing parameters used in compensating for aberrations in HDXRD measurements, in accordance with an embodiment of the present invention.

FIG. 8 is a ray diagram showing parameters used in compensating for aberrations in HDXRD measurements, in accordance with an embodiment of the present invention. Whereas the calibration computations described above assume that all rays in incident beam 26 are focused to a single point on sample 22, in practice aberrations of optics 32 cause some incident rays 90 to deviate from an ideal incident ray 94 at the same angle $A+\alpha$. Consequently, a corresponding diffracted ray 92 deviates by a commensurate amount from an ideal diffracted ray 96. The amount of deviation of the incident ray is a function of the ray angle, which is expressed in terms of the aberration $a(\alpha)$. This aberration results in a corresponding displacement of the focal point on the sample: $s(\alpha) = a(\alpha)/\sin(A+\alpha)$. This linear displacement is indistinguishable at detector array 42 from an equivalent angular shift of diffracted ray 92 by an amount:

$$\delta(\alpha) = s(\alpha)\sin(B+\beta)/D \quad (6)$$

wherein D is the focus-detector distance.

Figure 9:
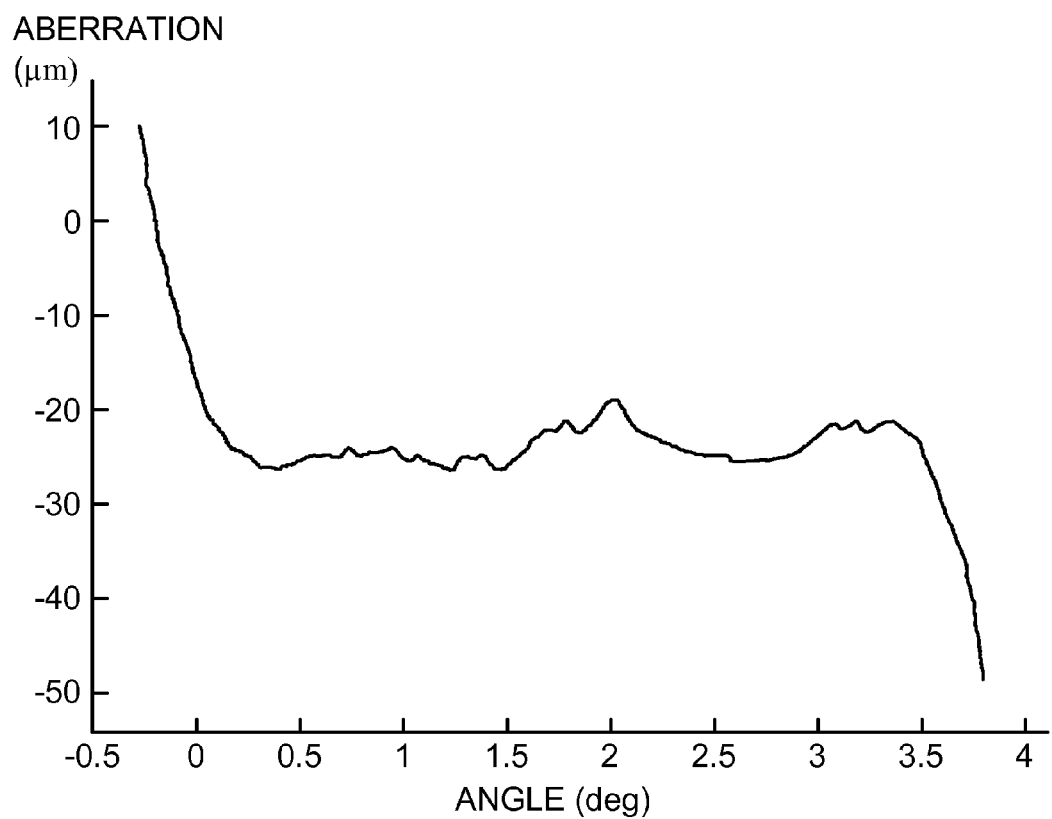
FIG. 9 is a plot of aberration measured as a function of angle in an X-ray beam used in a metrology system, in accordance with an embodiment of the present invention.

FIG. 9 is a plot of aberration-related shift $s(\alpha)$, measured as a function of angle in beam 28 emitted by X-ray source 26, in accordance with an embodiment of the present invention. The aberration measurements can be made in a similar fashion to the measurement of angle deviation described above, by performing a source scan and detecting changes in the position of a strong diffraction peak, such as substrate peak 60, after removing any displacement due to the surface of the sample not being exactly on the center of rotation of the source axis. Alternatively, other methods that are known in the art may be used to measure the aberrations. The plot in the figure shows the aberration in terms of the deviation of the measured location of the X-ray beam focus, as a function of the angle of incidence of the X-rays, relative to the ideal location. Over the central part of the scan shown in the figure, the deviation among the pixels is on the order of several microns.

The deviation of the focal location due to aberrations can be treated as a variation in the angular step size from pixel to pixel. In other words, the angular increment from pixel to pixel is not constant, but rather varies across detector array 42 by an amount related to the local aberration. To correct HRXRD measurements in system 20 for these aberration effects, processor 48 may compute and apply a correction factor in translating the pixel index into diffraction angle, giving the corrected angular position $\alpha_j$ corresponding to each pixel j:

$$\alpha_j = j\Delta\alpha - \delta(\alpha_j) \quad (7)$$

Here $\Delta\alpha = p/D$ is the angular pixel size (wherein p is the pitch of the detector elements). The correction factor $\delta$ is computed based on the calibration data, as defined by equation (6).

System Operation

Figure 10:
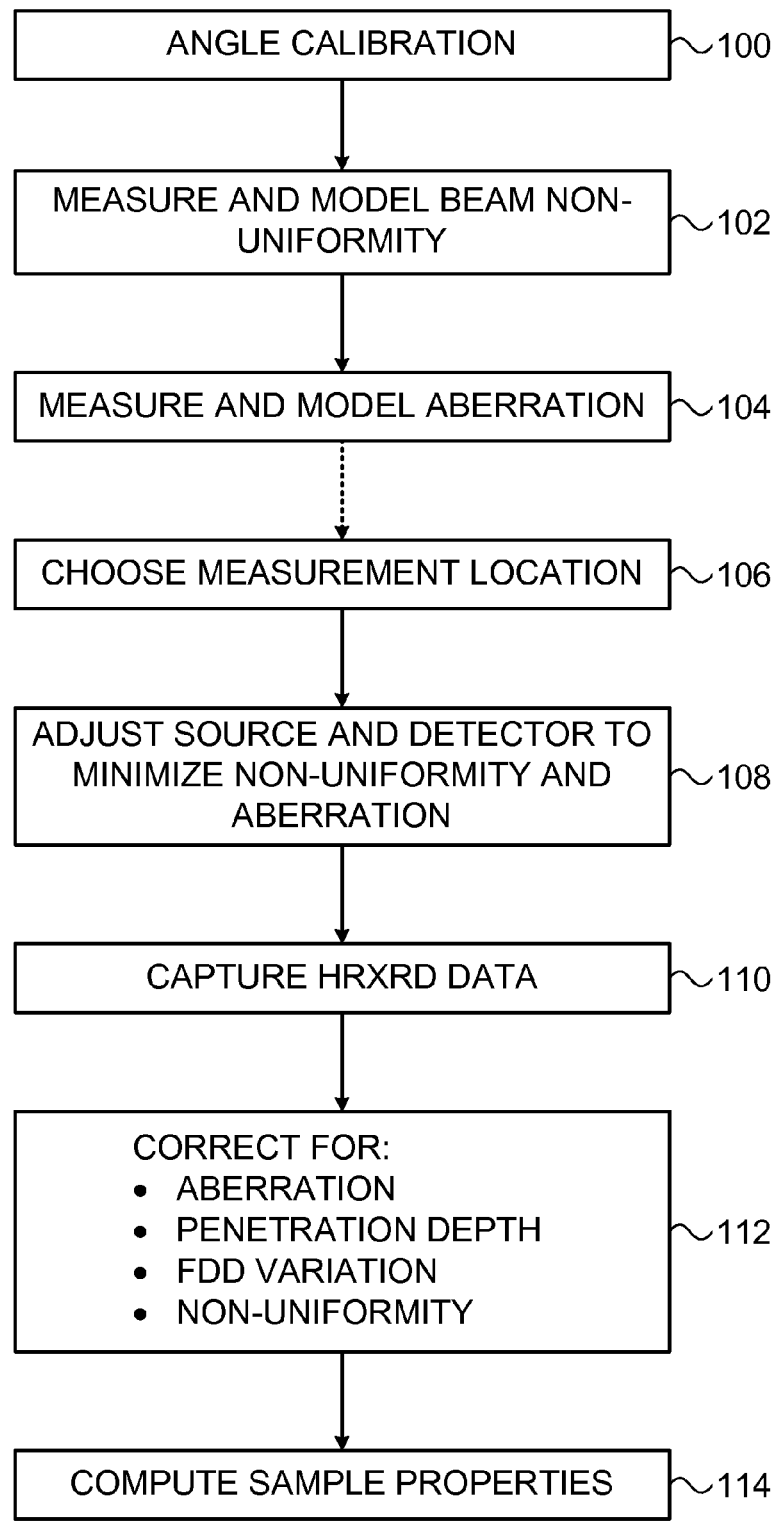
FIG. 10 is a flow chart that schematically illustrates a method for HRXRD measurement, in accordance with an embodiment of the present invention.

FIG. 10 is a flow chart that schematically illustrates a method for HRXRD measurement, in accordance with an embodiment of the present invention. The method is described hereinbelow, for the sake of convenience and clarity, with specific reference to the components of system 20. The principles of this method, however, may similarly be applied, mutatis mutandis, in other X-ray measurement systems and applications.

The method includes a calibration stage (steps 100-104), followed by a sample testing stage (steps 106-114), in which the calibration results are applied. The calibration stage starts with an angle calibration step 100, in which the elements of system 20 are operated to measure the angular errors in the system and the relationship between detector and source angles, as described above with reference to FIG. 7. This relationship is used to determine the angular shift of both the uniformity and aberration corrections that are applied in the sample testing stage.

The elements of system 20 are then operated to measure the degree of non-uniformity of beam 28 generated by source 26, at a non-uniformity calibration step 102. This measurement is applied in modeling the beam intensity variation with angle, so as to derive a correction function, as described above with reference to FIGS. 6A and 6B.

Additionally, the elements of system 20 are operated to measure spatial deviations of the beam from the ideal focus position as a function of angle, in an aberration calibration step 104. This measurement is used to derive an aberrations correction function, as described above with reference to FIGS. 8 and 9.

To begin the testing stage, a measurement location is chosen on sample 22, and stage 24 is operated to bring this location into the focus of beam 28 at the desired angle, at a location selection step 106. Source 26 and detector assembly 36 may then be adjusted to optimize the beam quality for the angle and location in question, at a setup optimization step 108. This step may be carried out manually, under direct control of an operator of system 20, or automatically, under control of processor 48. The "optimal" beam parameters in this context are those that minimize the non-uniformity and aberrations of the beam that is incident on the sample.

To adjust the source and detector locations, processor 48 may identify substrate peak 60 in the spectrum output by detector assembly 36. The processor may then operate motion assemblies 44 and 46 to move source 26 and detector assembly 36 so that peak 60 appears at a certain selected angular position. As some of the calibration and corrections functions described above are dependent on the source and detector angles A and B, processor 48 uses the adjusted source and detector angles to select the appropriate values of the calibration factors to be used subsequently.

Next, processor 48 actuates system 20 to capture HRXRD data from the selected location on sample 22, at a data capture step 110. The processor then corrects the spectral data for the deviations and non-uniformities described above, at a correction step 112. These corrections typically include variations in penetration depth (FIGS. 4-5), and beam non-uniformity (FIGS. 6A-6B), aberrations (FIGS. 8-9). Having performed the necessary corrections, processor 48 outputs corrected spectral data. The processor may apply these data in computing properties of sample 22, and particularly of thin film layers on the sample, at a property computation step 114.

Although the method of FIG. 10 involves a certain specific combination of corrections that are appropriate to system 20, it is not always necessary that all of these corrections be applied to HRXRD data. For example, it may in some circumstances be possible to omit certain corrections if they do not contribute significantly to the accuracy of a given measurement, and thus to perform only one or a few of the types of corrections that are described above. Alternatively, in other circumstances, it may be desirable to combine one or more of the above types of corrections with other calibration and data correction techniques that are known in the art.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for analysis, comprising:
   directing a converging beam of X-rays toward a surface of a sample;
   sensing the X-rays that are diffracted from the sample while resolving the sensed X-rays as a function of angle so as to generate a diffraction spectrum of the sample;
   calibrating a relation between an angle of the diffracted X-rays and an angular step size in the diffraction spectrum; and
   applying the calibrated relation to correct the angular scale of the diffraction spectrum in order to compensate for a non-uniform property of the converging beam.

2. The method according to claim 1, wherein correcting the diffraction spectrum comprises modifying intensities in the diffraction spectrum.

3. The method according to claim 2, wherein modifying the intensities comprises applying an intensity correction as a function of the angle of the sensed X-rays in order to compensate for a non-uniform intensity of the converging beam.

4. The method according to claim 1, and comprising analyzing the diffraction spectrum so as to identify a characteristic of the sample.

5. The method according to claim 4, wherein the sample includes an epitaxial layer that is formed over a substrate, and wherein the diffraction spectrum comprises at least a first diffraction peak due to the substrate and a second diffraction peak due to the epitaxial layer, and wherein analyzing the diffraction spectrum comprises applying the corrected diffraction spectrum in finding an angular distance between the first and second diffraction peaks.

6. The method according to claim 5, wherein applying the corrected diffraction spectrum comprises correcting the diffraction spectrum to account for a depth of penetration of the X-rays into the substrate.

7. The method according to claim 1, wherein sensing the X-rays comprises receiving and detecting the X-rays using an integrated circuit comprising a detector array and a readout circuit, wherein the readout circuit is covered by a non-metallic shield to prevent the diffracted X-rays from striking the readout circuit.

8. A method for analysis, comprising:
   directing a converging beam of X-rays toward a surface of a sample including an epitaxial layer that is formed over a substrate;
   simultaneously sensing the X-rays that are diffracted from the epitaxial layer and from the substrate while resolving the sensed X-rays as a function of angle so as to generate a diffraction spectrum comprising at least a first diffraction peak due to the substrate and a second diffraction peak due to the epitaxial layer; and
   finding an angular distance between the first and second diffraction peaks while correcting the diffraction spectrum to account for a depth of penetration of the X-rays into the substrate.

9. The method according to claim 8, wherein correcting the diffraction spectrum comprises computing a shift of the first diffraction peak due to the penetration as a function of angles of incidence and diffraction of the X-rays.

10. An apparatus for analysis, comprising:
    an X-ray source, which is configured to direct a converging beam of X-rays toward a surface of a sample;
    a detector assembly, which is configured to sense the X-rays that are diffracted from the sample while resolving the sensed X-rays as a function of angle so as to generate a diffraction spectrum of the sample; and
    a processor, which is configured to calibrate a relation between an angle of the diffracted X-rays and an angular step size in the diffraction spectrum, and to apply the calibrated relation to correct the angular scale of the diffraction spectrum in order to compensate for a non-uniform property of the converging beam.

11. The apparatus according to claim 10, wherein the processor is configured to correct the diffraction spectrum by modifying an intensity in the diffraction spectrum.

12. The apparatus according to claim 11, wherein the processor is configured to apply an intensity correction as a function of the angle of the sensed X-rays in order to compensate for a non-uniform intensity of the converging beam.

13. The apparatus according to claim 10, and wherein the processor is configured to analyze the diffraction spectrum so as to identify a characteristic of the sample.

14. The apparatus according to claim 13, wherein the sample includes an epitaxial layer that is formed over a substrate, and wherein the diffraction spectrum comprises at least a first diffraction peak due to the substrate and a second diffraction peak due to the epitaxial layer, and wherein the processor is configured to use the corrected diffraction spectrum in finding an angular distance between the first and second diffraction peaks.

15. The apparatus according to claim 14, wherein the processor is configured to correct the diffraction spectrum to account for a depth of penetration of the X-rays into the substrate.

16. The apparatus according to claim 10, wherein the X-ray source comprises an integrated circuit comprising a detector array and an readout circuit, wherein the readout circuit is covered by a non-metallic shield to prevent the diffracted X-rays from striking the readout circuit.

17. An apparatus for analysis, comprising:
    an X-ray source, which is configured to direct a converging beam of X-rays toward a surface of a sample including an epitaxial layer that is formed over a substrate;
    a detector assembly, which is configured to sense simultaneously the X-rays that are diffracted from the epitaxial layer and from the substrate while resolving the sensed X-rays as a function of angle so as to generate a diffraction spectrum comprising at least a first diffraction peak due to the substrate and a second diffraction peak due to the epitaxial layer; and
    a processor, which is configured to find an angular distance between the first and second diffraction peaks while correcting the diffraction spectrum to account for a depth of penetration of the X-rays into the substrate.

18. The apparatus according to claim 17, wherein the processor is configured to correct the diffraction spectrum by computing a shift of the first diffraction peak due to the penetration as a function of angles of incidence and diffraction of the X-rays.

* * * * *